US006407137B2

United States Patent
Shashoua

(10) Patent No.: US 6,407,137 B2
(45) Date of Patent: Jun. 18, 2002

(54) DOPAMINE ANALOG AMIDE

(75) Inventor: Victor E. Shashoua, Brookline, MA (US)

(73) Assignee: Protarga, Inc., King of Prussia, PA (US)

( * ) Notice: Subject to any disclaimer, the term of this patent is extended or adjusted under 35 U.S.C. 154(b) by 0 days.

(21) Appl. No.: 09/901,209

(22) Filed: Jul. 9, 2001

Related U.S. Application Data

(63) Continuation of application No. 09/450,310, filed on Nov. 29, 1999, now Pat. No. 6,258,836, which is a continuation-in-part of application No. 08/462,820, filed on Jun. 5, 1995, now Pat. No. 5,994,392, which is a continuation of application No. 08/080,675, filed on Jun. 21, 1993, now abandoned, which is a continuation of application No. 07/952,191, filed on Sep. 28, 1992, now abandoned, which is a continuation of application No. 07/577,329, filed on Sep. 4, 1990, now abandoned, which is a continuation-in-part of application No. 07/535,812, filed on Jun. 11, 1990, now abandoned, which is a continuation of application No. 07/315,134, filed on Feb. 24, 1989, now Pat. No. 4,933,324, which is a continuation-in-part of application No. 07/160,667, filed on Feb. 26, 1988, now Pat. No. 4,939,174.

(51) Int. Cl.$^7$ ............................................. A61K 3/18
(52) U.S. Cl. .................. 514/437; 514/452; 514/546; 514/549; 514/552; 514/678; 514/688; 549/1; 549/23; 549/26; 554/42; 554/78; 554/85; 554/101; 554/223; 554/234; 554/229; 568/303; 568/308; 568/335
(58) Field of Search ........................ 514/432, 437, 514/546, 549, 552, 678, 688; 549/1, 23, 26; 554/42, 78, 85, 101, 223, 234, 229; 568/303, 308, 335

(56) References Cited

U.S. PATENT DOCUMENTS 3,539,573 A    11/1970  Schmutz ................ 260/268
4,097,597 A    6/1978   Horrom et al. .......... 424/250

(List continued on next page.)

FOREIGN PATENT DOCUMENTS

| EP | 0 599 576 A 1 | 1/1994 |
| JP | 59-204175 | 11/1984 |

(List continued on next page.)

OTHER PUBLICATIONS

Baldessarini, et al., "Dopamine and Pathophysiology of Dyskinesis . . . ", Ann. Rev. Neurosci. 3:23–41 (1980).

Bourat, et al., "Long Chain Esters of Pipotiazine as Long-Acting Psychotropic Pro-Drug", Med. Chem. Proc. Int. Symp. 5th (1976) pp. 105–114.

Dhopeshwarker, G., "Fatty Acid Transport Through the Blood–Brain Barrier.", *Biochim. Biophys. Acta* 255:572–579.

(List continued on next page.)

*Primary Examiner*—Deborah D. Carr
(74) *Attorney, Agent, or Firm*—Wolf, Greenfield & Sacks P.C.

(57) ABSTRACT

The invention involves the formation of a prodrug from a fatty acid carrier and a neuroactive drug. The prodrug is stable in the environment of both the stomach and the bloodstream and may be delivered by ingestion. The prodrug passes readily through the blood brain barrier. Once in the central nervous system, the prodrug is hydrolyzed into the fatty acid carrier and the drug to release the drug. In a preferred embodiment, the carrier is 4, 7, 10, 13, 16, 19 docosahexa-enoic acid and the drug is dopamine. Both are normal components of the central nervous system. The covalent bond between the drug and the carrier preferably is an amide bond, which bond may survive the conditions in the stomach. Thus, the prodrug may be ingested and will not be hydrolyzed completely into the carrier molecule and drug molecule in the stomach.

18 Claims, 2 Drawing Sheets

U.S. PATENT DOCUMENTS

| | | | |
|---|---|---|---|
| 4,346,085 A | 8/1982 | Growdon et al. | 424/199 |
| 4,351,831 A | 9/1982 | Growden et al. | 424/199 |
| 4,407,744 A | 10/1983 | Young | 260/112 R |
| 4,550,109 A | 10/1985 | Folkers et al. | 514/249 |
| 4,554,272 A | 11/1985 | Bock et al. | 514/219 |
| 4,558,049 A | 12/1985 | Bernardi et al. | 514/234 |
| 4,636,494 A | 1/1987 | Growden et al. | 514/78 |
| 4,684,646 A | 8/1987 | Chang et al. | 514/221 |
| 4,788,063 A | 11/1988 | Fisher et al. | 424/449 |
| 4,902,505 A | 2/1990 | Pardridge et al. | 424/85.7 |
| 4,933,324 A | 6/1990 | Shashoua | 514/17 |
| 4,939,174 A | 7/1990 | Shashoua | 514/549 |
| 4,968,672 A | 11/1990 | Jacobson et al. | 514/46 |
| 5,112,596 A | 5/1992 | Malfroy-Camine | 424/2 |
| 5,112,863 A | 5/1992 | Hashimoto et al. | 514/534 |
| 5,116,624 A | 5/1992 | Horrobin et al. | 424/702 |
| 5,120,760 A | 6/1992 | Horrobin | 514/458 |
| 5,169,762 A | 12/1992 | Grey et al. | 424/702 |
| 5,169,764 A | 12/1992 | Shooter et al. | 514/538 |
| 5,284,876 A | 2/1994 | Shashoua | 514/549 |
| 5,516,800 A | 5/1996 | Horrobin | 514/560 |
| 5,545,719 A | 8/1996 | Shashoua | 530/345 |
| 5,604,198 A | 2/1997 | Poduslo et al. | 514/6 |
| 5,716,614 A | 2/1998 | Katz et al. | 424/94.3 |
| 5,795,909 A | 8/1998 | Shashoua et al. | 514/449 |
| 5,827,819 A | 10/1998 | Yatvin et al. | 514/2 |
| 5,919,815 A | 7/1999 | Bradley et al. | 514/449 |
| 5,955,459 A | 9/1999 | Bradley et al. | 514/220 |
| 5,977,174 A | 11/1999 | Bradley et al. | 514/549 |
| 5,994,392 A | 11/1999 | Shashoua | 514/437 |
| 6,005,004 A | 12/1999 | Katz et al. | 514/549 |
| 6,024,977 A | 2/2000 | Yatvin et al. | 424/450 |
| 6,107,499 A | 8/2000 | Shashoua | 554/78 |
| 6,153,653 A | 11/2000 | Shashoua | |
| 6,197,764 B1 | 3/2001 | Bradley et al. | |
| 6,225,444 B1 | 5/2001 | Shashoua | |

FOREIGN PATENT DOCUMENTS

| | | |
|---|---|---|
| JP | 61204136 | 11/1984 |
| JP | 6072868 | 3/1994 |
| WO | WO 85/00520 | 2/1985 |
| WO | WO 89/07938 | 9/1989 |
| WO | WO 92/20362 | 11/1992 |
| WO | WO 96/04001 | 2/1996 |
| WO | WO 96/22303 | 7/1996 |
| WO | WO 96/27380 | 9/1996 |
| WO | WO 98/17325 | 4/1998 |
| WO | 00/53231 * | 9/2000 |
| ZA | 96034333 A | 10/1996 |

OTHER PUBLICATIONS

D'Orlando, et al., "Citicoline (CDP–Choline): Mechanisms of Action and Effects in Ischemic Brain Injury", *Neurol. Res.* (1995) 17:281–284.

Garzon–Aburbeh, et al., "A Lymphotropic Product of L–Dopa:Synthesis" J. Med. Chem. 29:687–691 (1986).

Gunne, et al., "Oral Dyskinesia in Rats Following Brain Lesions and Neuroleptic Drug Administration", Psychopharmacology 77:134–139 (1982).

Hesse et al., "Inhibitory Effect of Cholesteryl–γ–Aminobutyrate", Neurolpharmacology, vol. 24, No. 2, pp. 139–146 (1985).

Hesse, et al., "Uptake in brain neurophysiological activity of two lipid esters of gamma–aminobutyric acid" *Neuropharmacol.* 27:6:637–40 (1988).

Higuchi et al., (Editors), Prodrugs as Novel Drug Delivery Systems, Acs Symposium Series, vol. 14, ACS, Washington, 1975, pp. 14–15.

Jacob, et al., "Synthesis, brain uptake and pharmacological properties of a glyceryl lipid containing GABA and the GABA–T inhibitor, gamma–vinyl–GABA," *J. Med. Chem.* 33:733–6 (1990).

Jacob, et al., γ–Aminobutyric Acid Esters.1. Synthesis . . . , Journal of Medicinal Chemistry, vol. 28, No. 1, pp 106–110 (1985).

Jacob, et al., γ–Aminobutyric Acid Esters.3. Synthesis, brain uptake and pharmacological properties of C–18 Glyceryl lipid esters of BAGA with varying degree of unsaturation, *J. Med. Chem.* 30:1573–6.

Jacobson, K., Adenosine analogs with covalently attached lipids have enhanced potency at A 1–adenosine receptors, *FEBS Letters* 225:1,2:97–102, (1987).

Konigstorfer et al., "Biosynthesis of Ependymins from Goldfish Brain", J. Biol. Chem., vol. 264 (23):13689–13692 (1989).

Konigstorfer et al., "Molecular Characterization Of An Ependymin Precursor from Goldfish Brain", J. Neurochem., 52:310–312 (1989).

Lohr, et al., "Neuroleptic–Induced Movement Disorders . . . ", Psychiatry, vol. 3, (1989).

Makino, et al., Chemical Abstracts, vol. 106, No. 12, (90177x) issued Mar. 23, 1987, "Pharmaceuticals Permeable to Blood–Brain Barrier".

Marder, S.R., *J. Clin Psychiatry* (supp 3), Management of Schizophrenia 57:9–13 (1996).

Nishio, et al., "Novel Water–soluble Derivatives of Docosahexaenoic Acid Increase Diacyl–Glycerol Production Mediated by Phosphatidylcholine–Specific Phospholipase C", *Proc. Soc. Exp. Biol. Med.* (1993) 203(2):200–208.

Schabitz, et al., "The effects of Prolonged Treatment with Citicoline in Temporary Experimental Focal Ischemia", *J. Neurol. Sci.*, (1996) 138(1–2):21–25 (Abstract).

Shashoua, V.E., "The Role of Brain Extracellular Proteins . . . ", *Cellular and Mol. Neurobiol.*, 5 (1/2):183–207 (1985).

Shashoua, et al., γ–Aminobutyric Acid Esters.1. Synthesis . . . , J. of Med. Chem., vol. 27, pp. 659–664 (1984).

Specter, R., "Fatty Acid Transport Through the Blood–Brain Barrier.", *J. of Neurochem.*, 50:2:639–643 (1988).

Shimazaki, N., et al., "N–$^6$–(2,2–Diphenylethyl)adenosine, a Novel Adenosine Receptor Agonist with Antipsychotic–like Activity", J. Med. Chem. 30:1709–1711 (1987).

Terasawa, et al., "Neurocalcin" a novel calcium binding protein from bovine brain *J. Biol. Chem.*, 267:27 (1992), pp. 19596–19599.

Yamamoto et al., "The Survival of Rat Cerebral Cortical Neurons in the Presence of Trophic APP Peptides" *J. Neurobiol.* 25, 585–594 (1994).

* cited by examiner

DOPAMINE ANALOG AMIDE

RELTAED APPLICATIONS

This application is a Continuation of prior application Ser. No. 09/450,310, filed on Nov. 29, 1999, entitled Dopamine Analog Amide and now U.S. Pat. No. 6,258,836 which is a continuation-in-part of Ser. No. 08/462,820, filed Jun. 5, 1995 now U.S. Pat. No. 5,994,392 which is a continuation of Ser. No. 08/080,675 filed Jun. 21, 1993 now abandoned which is a continuation of Ser. No. 07/952,191 filed on Sep. 28, 1992 now abandoned which is a continuation of Ser. No. 07/577,329 filed Sep. 4, 1990 now abandoned which is a continuation-in-part application of Ser. No. 07/535,812 filed Jun. 11, 1990, now ABN, which is a continuation of Ser. No. 07/315,134, filed Feb. 24, 1989, now patented, U.S. Pat. No. 4,933,324 which is a continuation-in-part application of Ser. No. 07/160,667, filed Feb. 26, 1988, now patented U.S. Pat. No. 4,939,174. The contents of all of the above-identified applications are hereby incorporated by reference.

The contents of co-pending application Ser. Nos. 07/517,158 and 07/517,159 both filed on May 1, 1990, now pending, are also expressly incorporated by reference.

BACKGROUND OF THE INVENTION

This invention relates in general to the fields of medicine, pharmacology and biochemistry, and more particularly to prodrugs capable of delivering a drug across the blood brain barrier including a prodrug made of a fatty acid-dopamine conjugate that is effective as an appetite-suppressant.

There are many obstacles to developing treatments which allow the delivery of a drug to an active site in the body. Ingestion of a drug often is not possible because many drugs will not survive the environment of the stomach. Thus, easy and safe self-administration of many drugs is not available. A drug, of course, may be injected directly into the blood stream of a patient. However, because some drugs do not survive for very long in the bloodstream, frequent injections at great inconvenience to a patient may be necessary. The inability of a drug to survive in the bloodstream may be overcome in certain instances by increasing the dosage or by increasing the frequency of administration. However, increasing the dosage can result in undesirable side effects and increasing the frequency of administration only adds inconvenience.

The delivery of a neuroactive drug to the central nervous system (CNS) via the bloodstream involves an extraordinary obstacle; the drug must be capable of crossing the blood brain barrier. The blood brain barrier may loosely be regarded as a biological exclusion barrier involving both passive and active transport, which barrier controls the exchange of materials between the plasma and the central nervous system. Many drug substances are unable to pass through this barrier in efficacious amounts or at all. Thus, there is a serious need for a mechanism for introducing a drug across the blood brain barrier and into the CNS.

Efforts have been taken to enhance the ability of certain drugs to pass through the blood brain barrier. Investigators have attempted to mask the polar groups of a drug to produce more lipophilic derivatives, as lipophilic compounds are believed to cross the blood brain barrier more readily than hydrophilic compounds. For example, diacetyl and triacetyl esters of dopamine and norepinephrine have been made to mask the hydroxyl groups of these compounds and produce more lipophilic derivatives. This investigator has formed an ester bond between γ-aminobutyric acid, a drug which is unable to cross the blood brain barrier, and a "carrier" molecule having an enhanced ability to cross the blood brain barrier. The carrier-drug conjugate shares with the carrier the ability to cross the blood brain barrier. Once in the CNS, the conjugate itself may be active. However, it is believed that the ester bond between the carrier and drug is broken in the CNS to release the drug in its native form. This may occur due to the general presence of active, non-specific esterases throughout the CNS.

Appetite-suppressant drugs have been sought for many years. Dopamine is believed to be involved in the neuropathways responsible for appetite-suppression. Dopamine itself is not used as an appetite-suppressant because it does not readily cross the blood brain barrier. Drugs which closely resemble the structure of dopamine and which will cross the blood brain barrier have been used with some success as alternatives to dopamine.

The most widely used appetite-suppressant drugs are generally based on derivatives of amphetamine, which structurally resembles dopamine and has some properties which correspond to a dopamine agonist. Unlike dopamine, sufficient uptake of amphetamines across the blood brain barrier does occur to produce a biological effect. However, amphetamines have many serious cardiovascular and neuropsychiatric side effects, as well as a tendency to develop tolerance, the increasing resistance to the usual effect of the drug over time. At worst, tolerance to a drug renders the drug useless. At best, tolerance generally encourages the use of higher drug doses, increasing the possibility of undesirable side effects. In animal tests, tolerance to certain of these amphetamine derivatives has been shown to develop within one day after one dose. Using amphetamine itself, tolerance has been shown to develop within 3–15 days.

Dopamine is also known to play a crucial role in several neurologically related disorders. For example, Parkinsonism is a striatal dopamine deficiency. Because dopamine (and related catacholamines) essentially does not cross the blood brain barrier Parkinsonism is treated with L-Dopa, a precursor to Dopamine. This treatment, however, is at the expense of a wide variety of undesireable side effects, including hallucination. Dopamine agonists which are used in the treatment of hyperprolactinemia associated with pituitary adenomas or amenorrhea also induce undesireable side effects. Thus, there is a serious need for delivering dopamine itself or dopaminergic agents directly to the brain.

SUMMARY OF THE INVENTION

The invention involves the formation of a prodrug from a fatty acid carrier and a drug. The prodrug is believed to be stable in the environment of both the stomach and the bloodstream and may be delivered by ingestion. The prodrug passes readily through the blood brain barrier. The prodrug has a brain penetration index of at least two times the brain penetration index of the drug alone. Once in the central nervous system, the prodrug, which preferably is inactive, is hydrolyzed into the fatty acid carrier and the drug. The carrier preferably is a normal component of the central nervous system and is inactive and harmless. The drug, once released from the fatty acid carrier, is active.

Preferably, the fatty acid carrier is a partially-saturated straight chain molecule having between about 16 and 26 carbon atoms, and more preferably 20 and 24 carbon atoms. Most preferably, the carrier is 4, 7, 10, 13, 16, 19 docosahexa-enoic acid.

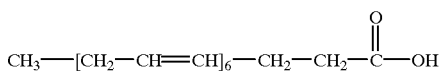

The covalent bond between the drug and the carrier preferably is an amide bond, which bond may survive the conditions in the stomach. Thus, the prodrug may be ingested and will not be hydrolyzed completely into the carrier molecule and drug molecule in the stomach.

The prodrugs of the invention preferably are formed of fatty acids conjugated to neurotransmitters, anti-aids substances, anti-cancer substances, antibiotics, peptides, anti-viral substances, anti-addiction substances, antipsychotic substances and anti-inflammatory substances. The prodrugs of the invention further may be provided in combination with pharmaceutically-acceptable carriers to form pharmaceutical preparations. Tablets and capsules are particularly preferred preparations.

In one preferred embodiment, the drug is dopamine, also a normal component of the central nervous system and the prodrug is

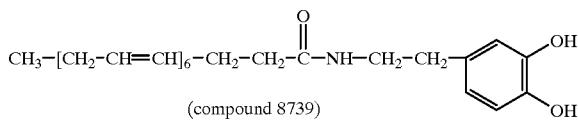

(compound 8739)

Compound 8739 may be expressed alternatively as

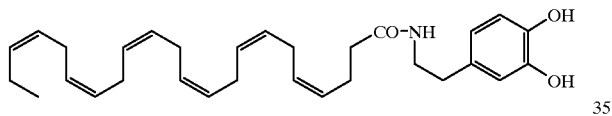

This compound has been found to be useful as an appetite-suppressant. It also is believed to have anti-psychotic properties. It has a brain penetration index of 33, a value eight times that of dopamine. It is inactive until it crosses the blood brain barrier and hydrolyzes to release dopamine into the central nervous system. The drug suppresses appetite without harmful side effects and without inducing tolerance. The prodrug also appears to be capable of delivering the dopamine preferentially into the synaptosomal membranes, the location of the drug action.

An object of the invention is to provide a carrier molecule capable of being combined with a drug to form a prodrug that will readily cross the blood brain barrier and allow release of the drug into the central nervous system.

Another object of the invention is to provide a prodrug that is stable in the environment of the stomach and in the bloodstream.

Another object of the invention is to provide pharmalogical compositions comprising amides of the carriers of the invention combined with drugs, including dopamine.

Another object of the invention is to provide a method for delivering a neuroactive drug, including dopamine, to the central nervous system.

Another object of the invention is to provide pharmaceutical preparations containing preselected doses of the prodrugs of the invention.

An object of the invention to provide an appetite-suppressant drug that will not induce tolerance and will not cause harmful side effects.

Another object of the invention is to provide an amide derivative of dopamine with biological activity useful in the regulation of appetite.

Yet a further object of the invention is to provide a method for treating neurological disorders in general, and specifically for introducing dopamine and dopaminergic agents into the brain to treat dopamine related disorders.

DETAILED DESCRIPTION OF THE PREFERRED EMBODIMENTS AND OF THE DRAWINGS

Figure 1:
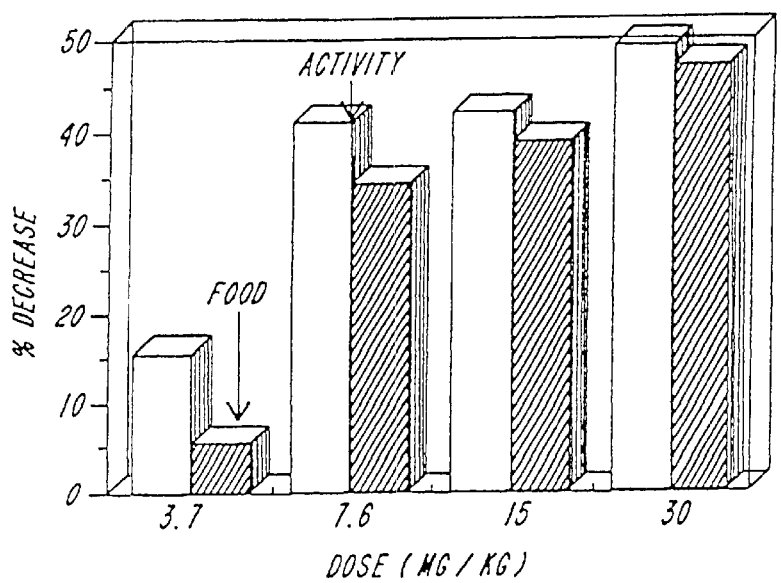
FIG. 1 is a graph showing the effect of the produrg of the preferred embodiment on motor activity and food intake of mice.

The most preferred embodiment of the invention is

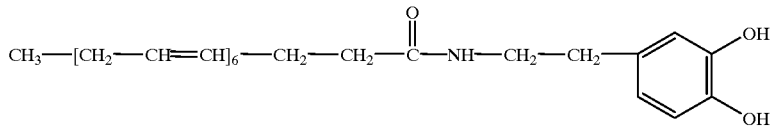

This compound has extraordinary and unexpected properties. This compound, hereinafter called compound 8739, is inactive until it crosses the blood brain barrier to release dopamine into the central nervous system (CNS). Unlike dopamine, compound 8739 survives sufficiently in the environment of the stomach and the bloodstream and therefore can be administered orally.

Compound 8739 has an enhanced ability to cross the blood brain barrier, with a brain penetration index (BPI) of about 33, as compared to about 4 for dopamine. It is inactive as a prodrug in that it does not bind to either D-1 or D-2 dopamine receptors. Rather, once in the central nervous system, dopamine is released as an active fragment of compound 8739. In addition, compound 8739 is taken up into the synaptosomal membranes preferentially, the synaptosomal membranes being the site of activity for the dopamine. This property may contribute to the compound's desirable properties.

Once dopamine is released as an active fragment, it produces effects on food intake and on general locomotor activity in mice in a dose-dependent manner. Food intake decreased by as much as 50% at the higher doses. Open field activity also decreased by about 50%, indicating that, unlike amphetimine, compound 8739 has a tranquilizing effect rather than an activity-enhancing effect.

Many of the undesirable side effects of amphetamines were absent. Compound 8739 failed to induce "stereotypy", failed to produce an effect on "circling behavior" of striatal lesioned rats, and failed to demonstrate any diverse effects on motor function or motivation in test animals. Remarkably, there was no indication of tolerance. Failure to induce tolerance was unexpected.

Another favorable property of compound 8739 was unexpected. Previous reports have demonstrated that fatty acids, including the fatty acid of compound 8739, induce swelling of the brain. Chan, P. H., Fishman, R. A., *SCIENCE*, Vol. 20, 358–360 (1978). Compound 8739 (and another prodrug compound made from a straight chain fatty acid having 20 carbon atoms and 4 double bonds), however, did not induce any swelling.

Experimental Data
Synthesis of the Compound 8739
Compound 8730 is synthesized as follows:

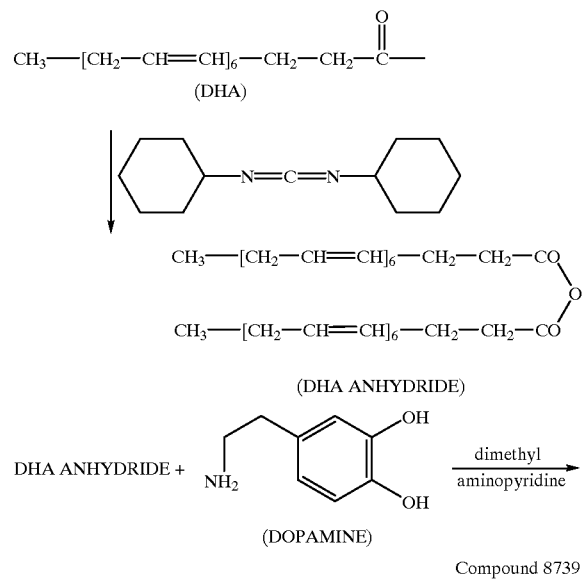

DHA is first converted to DHA anhydride in the presence of dicyclohexyl carbodiimide. This is then reacted with dopamine in the presence of 4-dimethylaminopyridine as the acid acceptor in tetrahydrofuran. In a typical experiment 300 mg of DHA (0.009 M) was dissolved in a mixture of 3 ml hexane and 4 ml benzene and stirred under nitrogen. Next, a solution of 0.00615 M of dicyclohexyl carbodiimide in 4 ml benzene (0.1267 g) was stirred together with the DHA for 3 hr at room temperature. A white precipitate of dicyclohexyl urea formed as the reaction proceeded. The dicyclohexyl urea was filtered off to give a clear solution of the anhydride in benzene. This was concentrated down to 2 ml in a rotary evaporator and diluted with 10 ml of tetrahydrofuran (dry). The freshly prepared anhydride was then added to a solution of dopamine hydrobromide (0.1053 g) (or 0.005 M) in the presence of 0.009 M of 4-diethylaminopyridine (0.098 g). The initially cloudy mixture after stirring for 30 min at room temperature gave a mixture of a clear liquid and a brown precipitate. At the end of the reaction, 0.2 ml of water was added to the mixture, and stirring was continued for an additional 30 min to completely hydrolyze any remaining unreacted anhydride. The liquid phase was isolated and evaporated to dryness to yield a brown viscous solid. This was then dissolved in 70% ethanol in water (25 ml), and the solution was then passed through a mixed-bed ion exchange resin containing a strong acidic resin based on polystyrene sulfonic acid and a strong basic resin based on quanternary amonium substituents such as tetramethyl amonimum hydroxide (RG501, Fisher Scientific, Cambridge, Mass.) using 90% ethanol in water as the eluent. This resin removes from the mixture unreacted dopamine, dimethylaminopyridine, as well as the liberated DHA molecule. The effluent from the column (a pale yellow solution) was then evaporated in a rotary evaporator to give a solid. The product was recrystallized from aqueous ethanol (yield=75%).

The structure of compound 8739 (III) was established by mass spectrometry. The major peak (95% of the compound) consisted of a product with a mass of 550. Fragment analysis by mass spectrometry and carbon, hydrogen, infrared, and NMR spectra confirmed the structure of compound 8739.

A trimethyl silyl derivative (compound IV) of the two hydroxyl groups of dopamine was also synthesized to further confirm the structure of compound 8739. This derivative was shown to have the correct mass of 608.

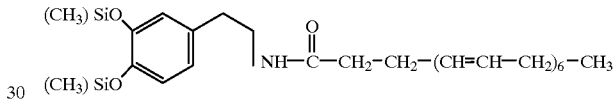

Compound IV

Compound 8739 was stored as a solution in ethanol (12 mg/ml) in the cold. Aliquots of this were evaported to dryness and dissolved in 15% propylene glycol in 0.1 M $NaHCO_3$ for use in biological activity tests.

Brain Uptake Studies

A brain penetration index (BPI) determination was used as a criterion for measuring the capacity of a compound to cross the blood brain barrier. Shashoua, V. E., Jacob, J. N., Ridge, R., Campbell, A. and Baldessarini, R. J., *J. Med. Chem.* 27, 659 (1984). The BPI is a measure of the uptake of a compound by the brain relative to its uptake by the liver. The liver is chosen as a reference since it is an organ which has no barrier to diffusable molecules present in the blood. Moreover, even if subcutaneous injections are used, the injected material tends to remain largely at the site of the injection and slowly diffuse into the circulation. Therefore, the amount of material in the liver will reflect the amount available rather than the initial dose injected.

Measurements of the quantity of the drug present in the brain and liver were measured at five minutes after a subcutaneous injection and were used to calculate the BPI, the equation being:

$$BPI=[brain]/[liver] \times 100$$

For these measurements, compound 8739 was synthesized from $^{14}C$-labeled dopamine. Thirty $\mu Ci$ of dopamine labeled hydrochloride was mixed with 0.1 mg of unlabeled dopamine hydrobromide and reacted with a two-fold excess of DHA anhydride. The reaction was run overnight; the product was then evaporated to dryness and dissolved in ethanol. The compound was identified as 8739 by its migration properties on thin-layer chromatography using chloroform:methanol as one solvent and dimethylformamide (DMF) as the other. The migration properties were equivalent to those of the unlabeled product.

$^{14}$C-labeled 8739 was dissolved in 15% propylene glycol in 0.1 M NaHCO$_3$ and then injected subcutaneously (s.c.) into male balb C mice (20±2 g). After 5 minutes the animals were sacrificed by cervical fracture and the brain and liver were dissected out, weighed and homogenized in 8 and 10 ml of Brain Protein Solvent (BPS) buffer, respectively [BPS=2% sodium dodecyl sulfate in 0.03 M Tris, 6 M urea, pH 7.6, 0.01 M EDTA and 0.14 N NaCl]. Aliquots were then counted for $^{14}$C content in 10 ml of a liquid scintillation fluid, Liquiscent (National Diagnostic Company, Somerville, N.J.) using a Beckman liquid scintillation counter. The $^{14}$C counts were then used to calculate the total quantity of compound 8739 present in the brain per gram of tissue as compared to that in the liver. The ratio of the amount in the brain as a percent of that present in liver was determined.

Results

TABLE I

| Compound | Brain (cpm/g) | Liver (cpm/g) | BPI Value (%) |
|---|---|---|---|
| 8739 | 1305 | 4300 | 30 |
| 8739 | 1297 | 3931 | 33 |
| Dopamine | | | 4 |
| D-glucose | | | 33 |

The results indicate that the brain uptake of compound 8739 is over eight-fold higher than the brain uptake for dopamine. Compound 8739 also compares favorably with glucose whch is reported in the literature to have a BPI index of 33.

Studies of the Pattern of Distribution of 8739 in Membranes of the Central Nervous System The utility of a drug may be determined by its ability to be taken up selectively by the particular regions of the brain upon which the drug acts. A study was made to determine the pattern of distribution of compound 8739 in the various membranes in the central nervous system. Approximately 2×10$^6$ counts of $^{14}$C-labeled 8739 in 0.3 ml of 15% propylene glycol in 0.1 M NaHCO$_3$ was injected subcutaneously into test mice (20±2 g). After 30 minutes the animals were sacrificed by cervical fracture; the brain was then removed and homogenized in 4 ml of isotonic medium (0.14 N NaCl, 0.03 M Tris pH 7.4 containing 1.5 rpm calcium acetate) according to the method of Whittaker (Whitaker V. P. Biochem J., 72 694–706 [1959]). The fraction P1 containing nuclear and cell membrane components was sedimented for 5 min at 2,500 rpm at 0° C. The supernatant containing the crude synaptosomal fraction was next centrifuged at 13,000 rpm for 30 min to yield a pellet containing the crude synaptosomal fraction (P2). P1 and P2 were then dissolved in BPS, and the amount of label and protein in each fraction was determined.

Results

TABLE II

| | CPM/mg Protein after 30 min of Uptake | | |
|---|---|---|---|
| Expt. No. | P$_1$ | P$_2$ | P$_2$/P$_1$ |
| | (Nuclear and Cell Membrane Fraction) | (Crude Synaptosomal Fraction) | |
| 1 | 2.7 | 5.2 | 1.9 |
| 2 | 2.7 | 5.6 | 2.1 |
| 3 | 4.19 | 12.5 | 2.9 |

As shown in Table II, the uptake of compound 8739 into the crude synaptosomal fraction (P2) was greater by a factor of an average of 2.3 than in the P1 fraction (nuclear and cell membrane fraction). This suggests that there is a preferential concentration of the compound into the synaptic fraction P2, indicating that 8739 is more highly associated with nerve endings, as would be expected from the natural distribution of DHA in lipid glycerides in such membranes.

Pharmacological Properties

Open-field motor activity measurement

The effect of compound 8739 on general motor activity was determined. The general motor activity of balb-c mice was measured in a Stoelting electronic activity monitor apparatus during a 90-min period following an intraperitoneal injection of the compound as a solution in 15% propylene glycol in 0.1 M NaHCO$_3$. A detailed description of the apparatus is reported in Stewart R. J., Campbell A., Spark G. and Balessarini R. J. Psychopharmacol. 60, 281 (1979).

The test group (six mice) received an i.p. injection of the drug in a vehicle (15% propylene glycol in 0.1 M NaHCO$_3$, a total volume of between about 1–0.3 ml.). The six control mice received the same volume of vehicle, but no drug. The results (Shown in FIG. 1,) are expressed as the percent decrease in open field activity for the test group versus the control group. The results indicate that compound 8739 depresses the activity of the mice by as much as 50%, demonstrating that compound 8739 is biologically active following its uptake into the brain. The response was dose dependant with higher doses of compound 8739 resulting in a greater decrease in general motor activity.

Food Consumption Measurements

The effect of compound 8739 on food consumption was determined for balb-c mice that were food deprived for 24 hr, with water freely available. The six test mice were given an i.p. injection of compound 8739 as a solution in 15% propylene glycol in 0.1 M NaHCO$_3$, a total volume of between about 0.1–0.3 ml. The six control mice received the same volume of vehicle, but no drug. The quantity of "mouse chow" eaten during the 60-min period following the injections was determined. The results, also shown in FIG. 1, are expressed as the percent decrease in food consumption for the test group versus the control group. The results indicate that compound 8739 is an appetite suppressant (40–50% decrease in food intake). The decrease was dose dependent, with higher doses of compound 8739 causing greater decrease in food intake. The same experiment was conducted using oral administration of compound 8739. The results were the same.

Figure 2:
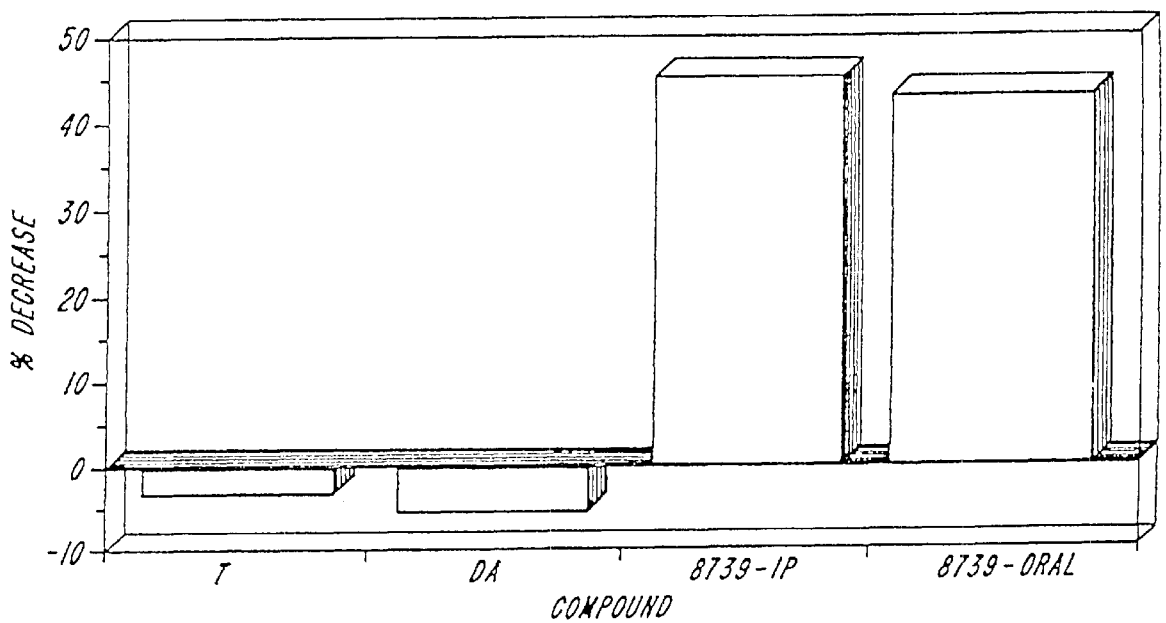
FIG. 2 is a graph comparing the effect on motor activity in mice of varying the mode of delivery of the prodrug of the preferred embodiment.

Determination of the Effect of Mode of Delivery of Compound 8739 on Open Field Activity The effects of the mode of delivery of Compound 8739 (oral vs. i.p.) on the general open-field activity of mice (n=6) was assessed. As shown in FIG. 2, the drug was as active when ingested as when injected. A 40–50% decrease in activity occurred when either delivery method was employed. No significant changes in open-field activity occurred when either the carrier molecule (T) or dopamine (DA) is administered at the same dose.

Evaluation of Circling Behavior

Dopamine agonists such as apomorphine and amphetamine cause circling behavior in animals with nigrostriatal lesions. Compound 8739 releases dopamine following proteolysis by central nervous system enzymes. It was expected that compound 8739 would cause circling behavior in animals with nigrostriatal lesions in a manner similar to that of dopamine agonists.

Unilateral nigrostriatal lesions in rats were produced by administering unilateral injections of 6-OH dopamine into the nigrostriatum pathway. Seven days later, these animals were i.p. injected with the test drugs and circling behavior was recorded as rotations per minute during a 30-min period in the test apparatus, Ungerstedt U. and Arbathnott G. W., *Brain Res.* 24, 485–493 (1970).

TABLE III

| COMPOUND | DOSE (mg/kg) | AVERAGE ROTATION SCORES (Rotations/minutes) | |
|---|---|---|---|
| | | Ipsilateral | Contralateral |
| Apomorphine | 0.1 | 0.1 | 4.8 |
| Apomorphine | 0.5 | 0 | 13.7 |
| Amphetamine | 3.0 | 2.5 | 0.4 |
| Amphetamine | 5.0 | 3.32 | 0.92 |
| 8739 | 34 | 0.08 | 0.05 |
| 8739 | 51 | 0.08 | 0.12 |
| Controls (uninjected) | | 0.10 | 0.12 |

Controls (uninjected) 0.10 0.12

Apomorphine produced a rapid circling behavior to the contralateral side of the lesion, whereas amphetamine caused circling rapidly to the ipsilateral lesion side. The enhanced contralateral rotations for apomorphine and ipsilateral rotations for amphetamine are consistent with the reported results for these dopaminme agonists. Compound 8739 did not evoke this behavior. Rather, the rate of circling was very low, approximately the same as that observed for uninjected controls. Thus it appears that compound 8739 does not evoke all of the effects (side effects) of dopamine agonists.

Self-stimulation Data

A self-stimulation test has been used to measure the capacity of a given pharmacological agent to inhibit rats from receiving self-induced electrical stimuli via electrodes implanted in their brains (lateral hypothalamus). Stellar J. R. and Stellar E., *The Neurobiology of Motivation and Reward*, Springer-Verlag, New York, 1985. Animals will press levers to receive a pulse of current from the implanted electrode at a rate dependent upon the quantity of current that is being delivered as a reward. It is believed that the reward obtained results from the release of dopamine caused by the electrical stimulation (Stellar J. R.). The intensity of the current is varied by raising the frequency at which 250 mV pulses (0.1 msec duration) are delivered during a 0.5-sec time span. A plot of the log of the frequency of the delivered pulses vs. the rate of level press for an animal gives the self-stimulation reward curve. Injections of drugs which have a neuroleptic-type or tranquilizing effect can depress the rate of self-stimulation, shifting the response to higher current deliveries. Pemozide can give a depressed rate by about 90%. Investigations of the efficacy of compound 8739 by this test showed that the compound had no effect on either the reward or the motor aspect of the self-stimulation parameters. This indicates that compound 8739, even though it is able to cause a decrease in the general motor activity of an animal, has no effect on the motivation or the capacity to press for the "current reward". The animal continues to press the lever at the rate equivalent to a non-injected control or one receiving the vehicle alone. Thus, compound 8739 does not produce yet another effect (side effect) characteristic of dopamine agonists.

Tests for Tolerance

The effects of daily i.p. injections of compound 8739 at a dose of 20 mg/kg on open field activity and food consumption was tested to determine whether tolerance to the drug was induced over time. The open field activity of six test mice and six control mice was monitored for five days. Then, the test mice were given i.p. injections of the drug in a vehicle and the control mice were given i.p. injections of the vehicle only. This regimen was carried out for a 21 day test period. At the end of the 21 days, the vehicle alone was given daily to both test and control mice and open field activity and food consumption was monitored for an additional six days.

Figure 3:
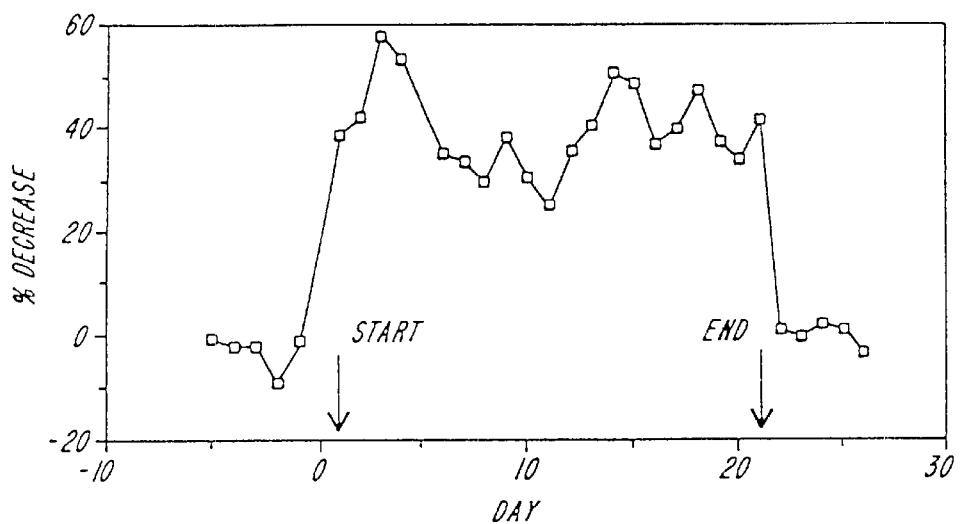
FIG. 3 is a graph showing the effect on motor activity in mice of long term administration of the prodrug of the preferred embodiment.

FIG. 3 plots the percent decrease in open field activity of the test mice (n=6) as compared to the controls (n=6). As shown in FIG. 3, the level of activity prior to injections was the same for both groups. Upon initation of injections, there was a 30% to 60% decrease in open field activity. This decrease remained fairly constant for the entire 21 days of injections indicating that no tolerance was induced by repeated injections during the test period. Beginning at day 22 and daily until day 27, vehicle alone was given to both groups. As shown in FIG. 3, activity returned to its predrug level when the drug administration was discontinued.

The effect of long-term administration of compound 8739 on the pattern of food consumption of mice was compared to the long-term effects of the administration of amphetamine. Daily i.p. injections of compound 8739 (20 mg/kg) were given to test animals and daily i.p. injections of amphetamine (2 mg/kg) were given to control animals for 21 days. 24 hours after the first injection and about every five days after that, the animals were food-deprived for 24 hours with water freely available, and then were tested for food consumption for one-hour beginning at five minutes after receiving their daily injection.

Figure 4:
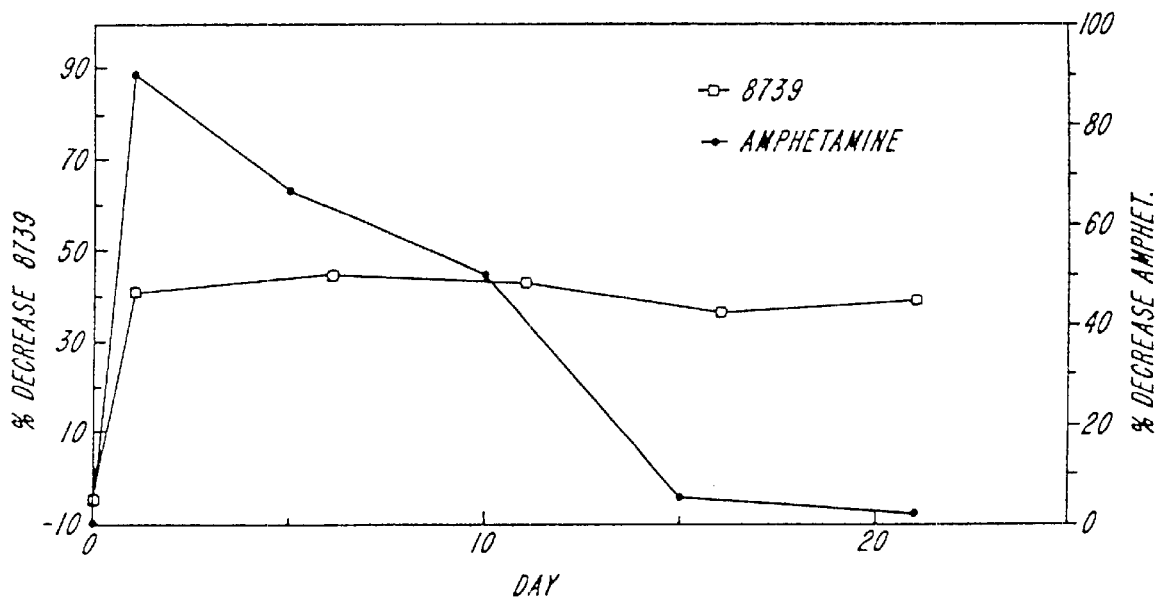
FIG. 4 is a graph comparing the effect on food intake in mice of long term administration of the prodrug of the perferred embodiment with amphetamine.

FIG. 4 plots the percent decrease in food consumption versus time. For amphetamine injected mice, the decrease in food intake due to the amphetamine virtually disappeared after 15 days indicating complete tolerance to the dosage employed. With compound 8739 injected mice, the approximately 40%–50% decrease in food intake persisted for the entire 21 day period indicating no tolerance had developed.

The pharmacological properties of compound 8739 appear to be characteristic of a partial dopamine agonist. Compound 8739 depresses the general motor activity and food intake behavior in mice. However, many of the properties which might be considered as "side effects" of dopamine agonists such as amphetamine and apomorphine are not obtained. Thus, circling behavior in nigrostriatal lesion to animals and motivational effects in self-stimulation experiments do not result following the administration of compound 8739.

Compound 8739 has been administered orally without any apparent loss in efficacy, and, therefore, is stable. Moreover, the compound does not bind to the dopamine receptors in receptor binding assays. Thus, the drug appears to be inactive until proteolysis releases the active dopamine. While the mechanism of action of the drug is not fully understood, and the inventor does not intend to be bound by any theory, it is believed that the localization of uptake into synaptic endings may cause site-specific release of the active dopamine from the prodrug. Such site-specific release could be responsible for some of the favorable properties of the drug. Further, that the carrier and drug are natural constituents of the CNS may contribute to compound 8739's desirable properties.

The invention is not limited to the foregoing description of the preferred embodiment. Thus, it is contemplated that the specific carrier described in the preferred embodiment and other carriers of the invention described in greater detail below are capable of being linked by an amide bond or otherwise to other drugs including other neurotransmitters, analogues of neurotransmitters including analogues of dopamine and other neuroactive substances to facilitate the delivery of the substance across the blood brain barrier and into the CNS. The term drug thus is intended to include agents that may be used on or administered to animals as an aid in diagnosis, treatment or prevention of disease or other abnormal conditions, for relief of pain or suffering, or to control, affect, maintain or improve a physiological or pathological condition. The term animal is intended to include those animals having central nervous system, and particularly those with a blood brain barrier and susceptible to the problems encountered when attempting to transport drugs across the blood brain barrier. Examples of amimals includes mammals, e.g. humans, domestic household, sport or farm animals such as sheep, goats, cattle, horses, mice, rats, guinea pigs, fish, aviens, reptiles, and zoo animals.

The preferred carrier has been coupled, for example, to a Met-enkephalin derivative of the following formula YGGFMK, in which the carrier is coupled via a peptide bond to the gamma amino group of lysine (K). This compound, when injected into mice at a dose of 20 mg/kg body weight, was effective as an analgesic at a tenfold lower dose as compared to the carrier free Met-enkephalin (Paw Lift Latency Hotplate Test). The preferred carrier has also been coupled via an amide bond to the free amino group of norepinephrin. This compound had an eightfold higher BPI than norepinephirn.

Classes of drugs which are intended to be included within this invention include neurotransmitters, anorectic compounds, anti-aids substances, anti-cancer substances, antibiotics, drugs effecting adenosine concentrations, adrenergics, cholinergics, benzodiazepines, drugs effecting cocaine receptors, drugs effecting cyclic nucleotide pathways, dopaminergics, enzyme inhibitors, excitatory amino acids, GABA-ergics, histaminergics, ion channel modulators, neurotoxins, opioids, drugs effecting PCP/ sigma receptors, cyrotonergics, hypnotics, psychic energizers, tranquilizers, benzodiazepines, anti-convulsants, muscle relaxants, anti-parkinson agents, anti-hypertensives, analgesics, anti-pyretics and anti-inflammatory agents, local anesthetics, anti-spasmodics and muscle contractants, prostaglandins, anti-bacterials, anti-septics, antidepressants, anti-migraine preparations, central nervous system stimulants, imaging agents, specific targeting agents, proteins, peptides, anti-viral agents, anti-psychotic agents, anti-addiction agents and anti-emetics.

Neurotransmitters are substances which are released from a neuron on excitation and travel to either inhibit or excite a target cell. Examples of neurotransmitters include dopamine, serotonin, γ-aminobutyric acid, norepinephrine, histamine, acetylcholine, and epinephrine.

Neuroactive amino acids include amino acids having at least some activity in the brain. Examples of neuroactive amino acids include glycine, aspartic acid, glutamic acid and taurine.

Anorectic compounds are substances which reduce or diminsh appetite. Examples of such compounds include amphetamine, phefluoramine, and diethylpropion. Although the CNS uptake of the anorectic compounds is satisfactory, when these compounds are coupled to the preferred carriers localized delivery of these compounds into the synaptosomal membranes of the CNS is facilitated.

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir (acyclovir), phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone caproate, medroxyprogesterone acetate, megestrol acetate, diethylstilbestrol, ethinyl estradiol, tamoxifen, testosterone propionate, fluoxymesterone, vinblastine (VLB), vincristine, vindesine, etoposide, teniposide, dactinomycin (actinomycin D), daunorubicin (daunomycin; rubidomycin), doxorubicin, bleomycin, plicamycin (mithramycin), mitomycin (mitomycin C), -asparaginase, hydroxyurea, procarbazine (N-methylhydrazine, MIH), mitotane, aminoglutethimide, mechlorethamine, cyclophosphamide, melphalan (-sarcolysin), uracil mustard, chlorambucil, busulfan, carmustine (BCNU), lomusline (CCNU), semustine (methyl-CCNU), streptuzocin (steptozotocin), dacarbazine (DTIC: dimethyltriazenomidazolecarboxamide), methotrexate (amethopterin), fluorouracil (5-fluorouracil: 5-FU), cytarabine (cytosine arabinoxide), mercaptopurine (6-mercaptopurine: 6-MP), thioguanine (6-thioguanine: TG).

Antibiotics are art recognized and are substances which inhibit the growth of or kill microorganisms. Antibiotics can be produced synthetically or by microorganisms. Examples of antibiotics include pennicillin, tetracycline, minocycline, doxycycline, vanomycin, bacitracin, kanamycin, neomycin, erythromicin and cephalosporins. Examples of cephalosporins include cephalothin (keflin, seffin), cephapirin (cefadyl), cefazolin (ancef, kefzol), cephalexin (keflex), cephradine (anspor, velosef), cefadroxil (duricef, ultracef), cefamandole (mandol), cefoxitin (mefoxin), cefaclor (ceclor), cefuroxime (zinacef), cefonicid (monocid), ceforanide (precef), cefotaxime (claforan), moxalactam (moxam), ceftizoxime (cefizox), ceftriaxone (rocephin), and cefoperazone (cefobid).

Drugs effecting adenosine concentration include both adenosine agonists and adenosine antagonists. Examples of adenosine agonists include adenosine, adenosine amine congener (ADAC), $N^6$-benzyladenosine, 2-chloroadenosine, 2-phenylamino adenosine (CV-1808), $N^6$-cyclohexyladenosine (CHA), $N^6$-cyclopentyladenosine (CPA), 5'-(N-cyclopropyl)carboxamidoadenosine, 1-deaza-2-chloro-$N^6$-cyclopentyladenosine, $N^6$-[20(3,5-dimethoxyphenyl)-2-(2-methylphenyl)]adenosine (DPMA), $N^6$-(2S)-[2-endo-norbornyl]adenosine (ENBA), 5'-N-ethylcarboxamidoadenosine (NECA), $N^6$-methyladenosine, 5'-N-methylcarboxamidoadenosine, 1-methylisoguanosine, 2-methylthio-ATP, $N^6$-phenyladenosine, $N^6$-phenylethyladenosine, $N^6$-(2-phenylisopropyl) adenosine R(−) isomer, and S(+)-$N^6$-(2-phenylisopropyl) adenosine.

Adenosine antagonists include aminophylline, 7-(β-chloroethyl)theophylline, 8-cyclopentyl-1,3-dimethylxanthine, 8-cyclopentyl-1,3-dipropylxanthine, 1,3-diethyl-8-phenylxanthine, 1,3-dimethylxanthine (theophylline), 1,7-dimethylxanthine (paraxanthine), 3,7-dimethylxanthine (theobromine), 1,3-dipropyl-7-methylxanthine, 1,3-dipropyl-8-p-sulfophenylxanthine, 7-(β-hydroxyethyl)theophylline, 3-isobutyl-1-methylxanthne (IBMX), 1,3-dipropyl-8-(2-amino-4-chlorophenyl)-xanthine (PACPX), 8-phenyltheophylline, 3-(n-propyl)-xanthine (enprofylline), 8-(p-sulfophenyl)-theophylline, 1,3,7-trimethylxanthine (caffeine), xanthine amine congener (XAC). Other drugs effecting adenosine concentrations include (R)-2-azido-$N^6$-p-hydroxyphenylisopropyl-adenosine (AHPIA), and dipyridamole.

Adrenergics are compounds that are agonists or antagonists of substances capable of stimulating or activating nerve systems that are responsive to norephinephrine and ephinephrine. Adrenergics include both adrenergic agonists and antagonists. Examples of adrenergic agonists include albuterol hemisulfate (salbutamol), p-aminoclonidine HCl, 4-[3-[(1,1-dimethylethyl)amino]-2-hydroxypropoxy]-1,3-dihydro-2H-benzimidazol-2-one hydrochloride, clonidine HCl, ephedrine HCl,(−)-, epinephrine bitartrate, 6-fluoronorepinephrine HCl, isoproterenol bitartrate,(−)-, isoproterenol bitartrate,(+)-, isoproterenol HCl,(±)-, norepinephrine HCl, octopamine,(±)-, and p-iodoclonidine HCl.

Examples of adrenergic antagonists include alprenolol HCl, bromoacetyl alprenolol methane (BAAM), benextramine HCl, benoxathian HCl, efaroxan, idazoxan, phenoxybenzamine HCl, phentolamine mesylate, pindolol, prazosin HCl, propranolol HCl,(−)-, propranolol HCl,(+)-, propranolol HCl,(±)-, rauwolscine HCl, 2-[2-(2-methoxy-1,4-benzodioxanyl)]imidazoline HCl, 2-(2,6-dimethoxyphenoxyethyl)aminomethyl-1,4-benzodioxane hydrochloride, yohimbine HCl. Other adrenergics include amphetamine sulfate,(+)-, amphetamine sulfate,(−)-, p-azidoclonidine oxalate, bretylium tosylate, chloroethylclonidine HCl, diethylpropion HCl, N-(2-chlorethyl)-N-ethyl-2-bromobenzylamine hydrochloride, metanephrine HCl, methamphetamine HCl,(+)-, methamphetamine HCl,(−)-, 4-hydroxy-3-methoxyphenylglycol piperazine salt,3-methoxy-4-hydroxy-phenylglycol piperazine salt, 4-hydroxy-3-methoxyphenylglycol-4-sulfate potassium salt, 3-methoxy-4-hydroxyphenylglycol-4-sulfate potassium salt, normetanephrine HCl, pindobind,(±)-, prazobind, threo-dihydroxyphenylserine(±)-, and xylamine HCl.

Cholinergics are compounds that are agonists or antagonists of substances capable of stimulating or activating nerve systems that are activated by acetyl choline. Cholinergics include both cholinergic agonists and cholinergic antagonists. Examples of cholinergic agonists include acetylcholine chloride, arecoline HBr, bethanechol chloride, carbachol, cis-dioxolane,(+)-, (4-hydroxy-2-butynyl)-1-trimethylammonium m-chlorocarbonilate chloride, methacholine chloride, metoclopramide HCl, muscarine chloride, (±)-, muscarine chloride(+)-, nicotine tartrate,S(−)-, cis-2-methyl-5-trimethylammoniummethyl-1,3-oxathiolane iodide (OXA-22), oxotremorine, oxotremorine sesquifumarate, and pilocarpine HCl,(+)-.

Examples of cholinergic antagonists include atropine sulfate, benztropine mesylate, 4-diphenylacetoxy-N-methylpiperidine methiodide, dexetimide HCl,S(+)-, levetimide HCl,R(−)-, ipratropium bromide, mecamylamine HCl, methoctramine HCl, pirenzepine HCl, RS(±)-quinuclidinyl benzilate, R(−)-quinuclidinyl benzilate, S(+)-quinuclidinyl benzilate, RS(±)-3-quinuclidinyl xanthene-9-carboxylate hemioxalate, scopolamine HBr,(−)-, scopolamine HBr,(+)-, scopolamine n-butyl bromide,(−)-, scopolamine methyl bromide,(−)-, scopolamine methyl bromide,(+)-, succinylcholine chloride, d-tubocurarine chloride, tetraethylammonium chloride. Other cholinergic drugs include acetylethylcholine mustard hydrochloride, N-aminodeanol HCl, eseroline fumarate, hemicholinium-3, vesamicol HCl,(±)-, vesamicol HCl,(−)-, and vesamicol HCl,(+)-.

Benzodiazepines are a type of tranquilizer having a common molecular structure of phenylthiazines and similar pharmacological activities such as anti-anxiety, muscle relaxing, sedative, and hypnotic effects. Benxodiazepines include benzodiazepine agonists, benzodiazepine antagonists and benzodiazepine inverse agonists. Examples of benzodiazepine agonists include chlordiazepoxide HCl, diazepam, flurazepam HCl, and flunitrazepam.

An example of a benzodiazepine antagonist is peripheral benzodiazepine antagonist and examples of benzodiazepine inverse agonists include ethyl β-carboline-3-carboxylate (β-CCE), methyl β-carboline-3-carboxylate (β-CCM), propyl β-carboline-3-carboxylate (β-CCP), 3-hydroxymethyl-β-carboline 3-HMC, methyl-6,7-dimethoxy-4-ethyl-β-carboline-3-carboxylate (DMCM), N-methyl-β-carboline-3-carboxamide (FG-7142). Other benzodiazepines include BZ receptor preparation, diazepam,desmethyl-, chlorazepate, diazepam, and oxazepam.

Drugs effecting cocaine receptors are substances which interact or interfere in some manner with a cocaine receptor. Examples of such drugs include buprenorphine, cocaine HCl, ecgonidine methyl ester, ecgonine HCl, CFT naphthalene disulfonate (WIN 35,428).

Drugs effecting cyclic nucleotide pathways are substances which interact or interfere in some manner with the cyclic nucleotide pathways. Examples of such drugs include forskolin, forskolin,7β-[γ-(morpholino)-butyryl]-, forskolin, 6β-[piperidino-propionyll-, and forskolin,1,9-dideoxy-.

Dopaminergics are drugs which in some manner effect, interact, or interfere with the dopaminergic pathways. The term is intended to include both dopamine agonists and dopamine antagonists. Dopamine agonists include N-allylnorapomorphine HBr,R(−)-, (±)-2-amino-5,6-dihydroxy-1,2,3,4-tetrahydronaphthalene hydrobromide (5,6-ADTN HBr), (±)-2-amino-5,6-dihydroxy-1,2,3,4-tetrahydronaphthalene hydrobromide (6,7-ADTN HBr), apocodeine HCl,R(−)-, apomorphine HCl,R(−)-, bromocriptine mesylate, (±)-6-chloro-7,8-dihydroxy-3-allyl-1-phenyl-2,3,4,5-tetrahydro-1H-3-benzazepine hydrobromide;6-chloro-N-allyl-SDK-38393 hydrobromide, (±)-2-dimethylamino-5,6-dihydroxy-1,2,3,4-tetrahydronaphthalene hydrobromide (M-7), (±)-2-dimethylamino-6,7-dihydroxy-1,2,3,4-tetrahydronaphthalene hydrobromide (TL-99), (±)-2-dipropylamino-6,7-dihydroxy-1,2,3,4-tetrahydronaphthalene hydrobromide, dipropyldopamine HBr, dopamine HCl, 2-hydroxyapomorphine HBr,R(−)-, R(−)-10,11-methylenedioxy-N-n-propylnoraporphine hydrochloride, N-methyldopamine HCl,(epinine), morphothebaine HCl, (±)-2-(N-phenylethyl-N-propyl)amino-5-hydroxytetralin hydrochloride, R(+)-3-(3-hydroxyphenyl)-N-propylpiperidine hydrochloride, S(−)-3-(3-hydroxyphenyl)-N-propylpiperidine hydrochloride, propylnorapomorphine HCl,R(−)- (NPA), quinpirole HCl, 1-phenyl-2,3,4,5-tetrahydro-(1H)-3-benzazepine-7,8-diol hydrochloride, R(+)-1-phenyl-2,3,4,5-tetrahydro-(1H)-3-benzazepine-7,8-diol hydrochloride, S(−)-1-phenyl-2,3,4,5-tetrahydro-(1H)-3-benzazepine-7,8-diol hyrdrochloride, (±)-7,8-dihydroxy-3-allyl-1-phenyl-2,3,4,5-tetrahydro-1H-3-benz azepine hydrochloride, tyramine HCl, and m-tyramine HCl.

Dopamine antagonists include amoxapine, apomorphine HCl,S(+)-, azidoclebopride, bulbocapnine,(+)-, butaclamol HCl,(+)-, butaclamol HCl,(−)-, domperidone, 1-ethoxycarbonyl-2-ethoxy-1,2-dihydroquinoline, eticlopride HCl,S(−)-, eticlopride HCl,R(+)-, fluphenazine HCl, flupentixol,cis(Z)-, fluspirilene, haloperidol, haloperidol, chlorinated analog, metoclopramide HCl, pimozide, prochlorperazine dimaleate, propylnorapomorphine HCl,S(+)-(NPA), R(+)-7-chloro-8-hydroxy-3-methyl-1-phenyl-2,3,4,5-tetra-hydro-1H-3-benzazepine hydrochloride, S(−)-7-chloro-8-hydroxy-3-methyl-1-phenyl-2,3,4,5-tetrahydro-1H-3-benzazepine hydrochloride, (±)-7-bromo-8-hydroxy-3-methyl-1-phenyl-2,3,4,5-tetrahydro-1H-3-benzazepine hydrochloride, spiperone HCl, sulpiride,(±)-, sulpiride,S (−)-, sulDiride,R(+)-, thiothixine HCl, trifluoperazine HCl, trifluoperidol HCl, thioridazine. Other dopaminergics include amantadine HCl, amfonelic acid, bupropion HCl, γ-butyrolactone, chloroethylnorapomorphine HCl, L-3,4-dihydroxyphenylalanine (L-DOPA), D-3,4-dihydroxyphenylalanine (DOPA,D-), L-3,4-dihydroxyphenylalanine methyl ester hydrochloride, 3,4-dihydroxyphenylacetic acid (DOPAC), 1-[2-(Bis(4-fluorophenyl)methoxy]ethyl]-4-[3-phenylpropyl]piperaz ine dihydrochloride, haloperidol metabolite I, haloperidol metabolite II, haloperidol metabolite III, homovanillic acid, 3-O-methyldopamine HCl, 4-O-methyldopamine HCl, nomifensine, reserpine, and tetrahydro-L-biopterin HCl.

Enzyme inhibitors are substances which inhibit an enzymatic reaction. Examples of enzyme inhibitors include edrophonium chloride, N-methylphysostigmine,(−)-, neostigmine bromide, physostigmine sulfate, tacrine HCL (THA), tacrine,1-hydroxy maleate, iodotubercidin, p-bromotetramisole,(−)-, 10-(α-diethylaminopropionyl) phenothiazine hydrochloride (As-1397), calmidazolium chloride, hemicholinium-3, 3,5-dinitrocatechol (OR-486), diacylglycerol kinase inhibitor I (R59022), diacylglycerol kinase inhibitor II (R59949), 3-phenylpropargylamine, $N^6$-monomethyl-L-arginine acetate, carbidopa, 3-hydroxybenzylhydrazine HCl (NSD-1015), hydralazine HCl (apresoline), clorgyline HCl, deprenyl HCl,L(−)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride (CONH), (±)-2,3-dichloro-α-methylbenzylamine (DCMB),(LY-78335), 8,9-dichloro-2,3,4,5-tetrahydro-1H-2-benzazepine hydrochloride, p-aminoglutethimide,(±)-, p-aminoglutethimide tartrate,R(+)-, p-aminoglutethimide tartrate,S(−)-, 3-iodotyrosine,L-, α-methyltyrosine,L-, α-methyltyrosine,D L-, and allopurinol.

Excitatory amino acids are amino acids used to activate or excite neurons involved in the glutaminergic or aspartic acid stimulated pathways. Excitatory amino acids include both agonists and antagonists. Exictatory amino acid agonists include (R,S)-α-amino-3-hydroxy-5-methylisoxazole-4-propionic acid hydrobromide, (R,S)-α-amino-3-hydroxy-5-methylisoxazole-4-propionic acid, aspartic acid,L-, glutamic acid HCl,L-, glutamic acid diethyl ester HCl,L-, ibotenic acid, kainic acid, N-methyl-D-aspartic acid (NMDA), cis-piperidine-2,3-dicarboxylic acid, and quisqualic acid,(+)-.

Excitatory amino acid antagonists include 3-amino-1-hydroxy-2-pyrrolidone (HA-966), 7-chlorokynurenic acid, 6-cyano-7-nitroquinoxaline-2,3-dione, dextromethorphan HBr, dextrorphan, 6,7-dinitroquinoxaline-2,3-dione, 5-fluoroindole-2-carboxylic acid, kynurenic acid, 2-amino-3-phosphonopropionic acid (AP-3), (±)-2-amino-4-phosphonobutyric acid (AP-4), 2-amino-5-phosphonopentanoic acid (AP-5), (±)-2-amino-7-phosphonoheptanoic acid (AP-7), (±)-3-(2-carboxypiperazin-4-yl)-propyl-1-phosphonic acid, ketamine HCl, (+)-5-methyl-10,11-dihydro-5H-dibenzo[a,d] cyclohep-ten-5,10-imine hydrogen maleate, (−)-5-methyl-10,11-dihydro-5H-dibenzo[a,d]cyclohep-ten-5,10-imine hydrogen maleate.

GABA-ergics are substances capable of interacting in some manner with neurons that have gamma-aminobutyric acid receptors. GABA-ergics include both GABA agonists and GABA antagonists. Examples of GABA agonists include baclofen,(±)-, γ-aminobutyric acid (GABA), isoguvacine HCl, isonipecotic acid, kojic amine, muscimol HBr, piperidine-4-sulfonic acid, thiomuscimol HBr, and 4,5,6,7-tetrahydroisoxazolo[5,4-c]pyridin-3-ol HCl.

Examples of GABA antagonists include 5-aminovaleric acid HCl, bicuculline, bicuculline methchloride, bicuculline methbromide, bicuculline methiodide, 2-hydroxysaclofen, phaclofen, 2-(3-carboxypropyl)-3-amino-6-(4-methoxyphenyl)pyridazinium bromide. Other GABA-ergics include 4-aminopyridine, butylbicyclophosphorothionate (TBPS), GABA receptor preparation, guvacine HCl, cis-4-hydroxynipecotic acid, γ-hydroxybutyric acid, nipecotic acid,(±)-, pentylenetetrazole, picrotoxin, and 4,5,6,7-tetrahydroisoxazolo[4,5-c]pyridin-3-ol (THPO HBr).

Histaminergics are substances which interact or interfere in some manner with histamine and/or histamine receptors. Histaminergics include both histamine agonists and histamine antagonists. Histamine agonists include dimaprit, histamine HCl, histamine,α-methyl oxalate,R(−)-. Histamine antagonists include cimetidine, chlorpheniramine maleate, (±)-, chlorpheniramine maleate,(+)-, cyproheptadine HCl, ranitidine HCl, pyrilamine maleate. Other histaminergics include histidine HCl,L-, and histidine HCl,D-.

Ion channel modulators are compounds that modify the activity of receptors controlling the flow of ions into cells. Ion channel modulators include both ion channel activators and ion channel antagonists. An example of an ion channel activator includes 1,4-dihydro-2,6-dimethyl-5-nitro-4-[2-(trifluoromethyl)-phenyl]-3-pyridinecarboxylic acidmethyl ester. Examples of ion channel antagonists include amiloride HCl, amiloride,5-(N,N-dimethyl)HCl, amiloride,5-(N,N-hexamethylene)-, amiodarone HCl, benzamil HCl, bepridil HCl, clofilium tosylate, ω-conotoxin GVIA, cyproheptadine HCl, diltiazem HCl, R(+)-[(2-n-butyl-6,7-dichloro-2-cyclopentyl-2,3-dihydro-1-oxo-1H-inden-7-yl),oxy]acetic acid, flunarizine HCl, fluspirilene, R(+)-[(6,7-dichloro-2-cyclopentyl-2,3-dihydro-2-methyl-1-oxo-1H-inden-5-yl)-oxy]acetic acid, lidocaine N-ethyl iodide, methoxyverapamil HCl,(±)-, methoxyverapamil HCl,S(−)-, methoxyverapamil HCl,R(+)-, nifedipine, pimozide, ryanodine, 8-(diethylamino)octyl-3,4,5-trimethoxybenzoate hydrochloride, verapamil HCl,(±)-, verapamil HCl,S(−)-, verapamil HCl,R(+)-. Other ion channel modulators include calmidazolium chloride, fluphenazine N-mustard, phenoxybenzamine HCl, trifluoperazine HCl, N-(6-aminohexyl)-5-chloro-1-naphthalenesulfonamide hydrochloride, N-(4-aminobutyl)-5-chloro-2-naphthalenesulfonamide hydrochloride, D(+)-myo-inositor-1,4,5-triphosphate (synthetic), N-(2-guanidinoethyl)-5-isoquinolinesulfonamide hydrochloride, 1-(5-isoquinolinesulfonyl)-2-methylpiperazine kihydrochloride, N-[2-(methylamino)ethyl]-5-isoquinolinesulfonamide dihydrochloride, N-(2-aminoethyl)-5-isoquinolinesulfonamide dihydrochloride, diacylglycerol kinase inhibitor I (R59022), diacylglycerol kinase inhibitor II (R59949), and N-(n-heptyl)-5-chloro-1-naphthalenesulfonamide.

Neurotoxins are substances which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride acetyl AF-64. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4-phenyl-1,2,5,6-tetrahydropyridine HCl, 1-methyl-4-phenylpyridinium iodide. Other neurotoxins include L-β-methyl-α,β-diaminopropionic acid hydrochloride, (±)-β-methyl-α,β-diaminopropionic acid hydrochloride, L-β-oxalyl-α,β-diaminopropionic acid, and quinolinic acid.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimine HCl, buprenorphine, β-chlornaltrexamine 2HCl, β-funaltrexamione HCl, nalbuphine HCl, nalorphine HCl, naloxone HCl, naloxonazine, naltrexone HCl, and naltrindole HCl(NTI).

Drugs effecting PCP/Sigma receptors include both receptor agonists and receptor antagonists. Receptor agonists include N-allylnormetazocine HCl,(+)-(SKF-10047), N-allylnormetazocine HCl,(-)-, 1,3-Di(2-tolyl)guanidine (DTG), phencyclidine HCl, 1-[1-(2-thienyl)cyclohexyl] piperidine hydrochloride (TCP). Receptor antagonists include metaphit methanesulfonate, and R(+)-3-(3-hydroxyphenyl)-N-propylpiperidine hydrochloride.

Serotonergics are substances that interact or interfere in some manner with nerve cells having serotonin receptors. Serotonergics include serotonin agonists and other serotonergics. Serotonin agonists include carboxamidotryptamine maleate (5-CT), 1-(3-chlorophenyl)piperazine HCl, 7-trifluoromethyl-4(4-methyl-1-piperazinyl)-pyrrolo[1,2-a] quinosaline,1:2 maleate salt, dipropyl-5-carboxamidotryptamine (DP-5-CT), (±)-1-(2,5-dimethoxy-4-iodophenyl)-2-aminopropane HCl, (±)-1-(4-bromophenyl-2,5-dimethoxy)-2-aminopropane hydrobromide, 1-(2,5-dimethoxyphenyl)-2-aminopropane hydrochloride (DMA), (±-2-dipropylamino-8-hydroxy-1,2,3,4-tetrahydronaphthalene HBr,(±)-8-hydroxydipropylaminotetralin HBr, 5-methoxy-N,N-dimethyltryptamine hydrogen oxalate, 1-(2-methoxyphenyl) piperazine HCl, 5-methoxytryptamine HCl, 2-methylserotonin maleate, α-methylserotonin maleate, p-aminophenylethyl-m-trifluoromethylphenyl piperazine;4 [2-[4-[3-(trifluoromethyl)phenyl]-1-piperazinyl]ethyl] benzeneamine, 1-phenylbiguanide, quipazine maleate serotonin creatinine sulfate, serotonin HCl, serotonin oxalate, spiroxatrine, m-trifluoromethylphenylpiperazine hydrochloride, cyproheptadine HCl, 3-tropanyl-indole-3-carboxylate (ICS 205,930), 3-tropanyl-indole-3-carboxylate methiodide, ketanserin tartrate, 3-tropanyl-3,5-dichlorobenzoate (MDL-72222), metoclopramide HCl, mianserin HCl, 1-(1-naphthyl)piperazine HCl, pirenperone, propranolol HCl,S(-)-, propranolol HCl,R(+)-, propranolol HCl,(±)-, ritanserin, spiperone HCl, zacopride maleate. Other serotonergics include p-chlorophenylalanine, clomipramine HCl, fenfluramine,S(+)-, fenfluramine,R(-)-, 5-hydroxy-L-tryptophan, imipramine HCl, L-tryptophan, zacopride maleate,(±)-, and zimelidine HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarimides, diethyl isovaleramide, α-bromoisovaleryl urea, urethanes and disulfanes.

Psychic energizers are substances that raise the energy level of the brain, such as compounds that raise the level of ATP or inhibit its breakdown in nerve cells. Examples of psychic energizers include isocarboxazid, nialamide, phenelzine, imipramine, amitryptyline hydrochloride, tranylcypromine, pargylene, and protryptyline hydrochloride.

Tranquilizers are substances which provide a tranquilizing effect. Examples of tranquilizers include chloropromazine, promazine, fluphenzaine, reserpine, deserpidine, and meprobamate.

Anticonvulsants are substances which have an effect of preventing, reducing, or eliminating convulsions. Examples of such agents include primidone, phenytoin, valproate, Chk and ethosuximide.

Muscle relaxants and anti-parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Antihypertensives are substances capable of counteracting high blood pressure. Examples of such substances include α-methyldapa and the pivaloyloxyethyl ester of α-methyldapa.

Analgesics are substances capable of preventing, reducing, or relieving pain. Examples of analgesics include morphine sulfate, codeine sulfate, meperidine, and nalorphine.

Antipyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include procaine, lidocain, tetracaine and dibucaine.

Antispasmodics and muscle contractants are substances capable of preventing or relieving muscle spasms or contractions. Examples of such agents include atropine, scopolamine, oxyphenonium, and papaverine.

Prostaglandins are art recognized and are a class of naturally occurring chemically related, long-chain hydroxy fatty acids that have a variety of biological effects. Examples of such agents include E2, and E1.

Anti-bacterials are substances which destroy or suppress the growth or reproduction of bacteria. Examples of anti-bacterials include trimethoprin, sulfamethoxazole, cefoperazone, chloroamphenicol, polymycin, and metronidazole.

Antiseptics are substances capable of inhibiting the growth and development of microorganisms without necessarily destroying them. Examples of antiseptics include those discussed above as anti-bacterials and other sulfonamide substances.

Anti-depressants are substances capable of preventing or relieving depressant. Examples of anti-depressants include imipramine, amitriptyline, nortriptyline, protriptyline, desipramine, amoxapine, doxepin, maprotiline, tranylcypromine, phenelzine, and isocarboxazide.

Anti-migraine preparations are substances capable of preventing or relieving migraine headaches. Examples of such substances include ergotamine tartrate, caffeine, dihydroengotamine mesylate propanolol HCl, acetominophin, and salicylic acid.

Central nervous system stimulants are substances capable of stimulating the central nervous system. Examples of such substances include amphetamine, phenylalanine, picrotoxinin, and methylphenidate.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

The term protein is art-recognized and for purposes of this invention also encompasses peptides. Examples of proteins include antibodies, hormones, and growth factors, e.g. nerve growth factors and an example of a peptide includes nerve growth factor peptide.

The proteins or peptides may be any bioactive protein or peptide, naturally occurring or synthetic. The term peptide is intended to include the classes of peptides known as neuropeptides and regulatory peptides. Specific examples of such factors include growth hormone and growth hormone-releasing hormone, gonadotorpin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, alpha and beta melanocyte-stimulating hormones, peptide molecules which stimulate erythrocytes, leucocyte and immunocyte growth and function such as colony stimulating factors (CFS 1 and 2), erythropoitin and lymphokines (including interleukin I and II), angiotensin I and II, bradykinin, kallidin, adrenocorticotropic hormone, thyroid stimulating hormone, insulin, glucagon and the numerous analogues and congeners of the foregoing peptides. It should be understood that the term peptide is intended to include small proteins and particularly those molecules having on the order of about 100 amino acids or less. Other larger proteins are intended to be encompassed by the term protein.

The protein or peptide preferably has a molecular weight of less than about 5,000 and more preferably less than about 1,500.

Anti-viral agents are substances capable of destroying or suppressing the replication of viruses. Examples of anti-viral agents include α-methyl-l-adamantane methylamine (rimantadine), 1-β-D-ribofuranosyl-1,2,4-triazole-3 carboxamide (ribavirin), 9-[2-hydroxy-ethoxy]methylguanine (Acyclovir), adamantanamine, and 5-iodo-2'-deoxyuridine (Idoxuridine), adenine arabinoside (Vidarabine) and interferon, synthetic or naturally occuriing.

Anti-psychotic agents are substances which modify psychotic behavior. Examples of such agents include phenothiazines, butyrophenones and thioxanthenes.

Anti-emetics are substances which prevent or alleviate nausea or vomiting. An example of such a substance includes dramamine.

The examples discussed above may be listed in the salt or non-salt form but for purposes of this invention both forms are intended to be encompassed. Further, if a particular salt-form of a drug, e.g. naloxone HCl, is listed, other art recognized biologically accepted salts can be used in place of the listed salt-form. Examples of acceptable salts include hydrochlorides, hydrobromine, sulfate, laurelate, palmatate, phosphate, nitrate, borate, acetate, maleate, tartrate, oleate, salisilate, salts of metals, means or organic cations, e.g. quarternary ammonium.

This invention is also intended to encompass derivatives or equivalents of the above discussed drugs. A derivative is a drug which is structurally similar to the foregoing list of drugs and is capable of achieving the same or substantially the same function or activity. An equivalent is an agent capable of achieving the same or substantially the same intended function or activity.

The drug compound and carrier may be coupled using a variety of reactions involving treating the neuroactive compound (or a protected derivative thereof) having one, free hydroxyl or amino group with the corresponding fatty acid carrier or an activated derivative thereof. For example, a dopamine derivative having its two hydroxyl groups protected with acetonide may be reacted with the carrier in the presence of a water-removing compound such as dicyclohexyl carbodiimide in a solvent such as dioxane, tetrahydrofurane and methylpyrrolidone or N,N dimethylformamide at ambient temperature. The solvent then may be removed and the desired product may be extracted from the formed dicyclohexylurea using a suitable solvent such as methylene chloride. The protecting group then may be removed by treatment with a suitable acid such as 4N HCl in dioxane. The amine group of a neuroactive compound may be coupled to the carboxyl group of the carrier also by using the acid chloride or a low carbon ester derivative of the carrier and forming amide bonds by liberating HCl or an alcohol respectively. Drugs containing alcohol groups (OH) may be coupled via ester bonds to the fatty acid carrier by similar procedures as described above (e.g. using the anhydride derivative, the acid chloride derivative for the free acid of the carrier). Alternate couplings such as phosphoramide, sulfate, sulfonate, phosphate or urethane also may be used as will be recognized by one of ordinary skill in the art to coupled carrier molecules to drugs.

Amide bonds are preferred because they may survive the environment of the stomach and the prodrug may be administered orally. However, it should be recognized that bonds incapable of surviving the environment of the stomach such as an ester bond still may be used to link the carrier of the invention and a drug, with the resulting conjugate capable of crossing the blood brain barrier. Such a prodrug may be injected or protected from the environment of the stomach by, for example, coatings, well-known to those skilled in the art. Such a coating may be called for even in the presence of an amide bond between the carrier and the drug.

The compounds of the invention can be prepared in pharmaceutical preparations containing the compounds themselves and a pharmaceutically acceptable carrier. Such carriers include those that facilitate administration of the prodrug, prolong shelf life of the prodrug, allow a particular mode of administration of the prodrug, or provide or facilitate formulation of a particular dose of the prodrug. The pharmaceutically acceptable carrier may be solid or liquid. Examples of liquid carriers include water, an aqueous solution of non-toxic salts, such as sterile physiological solutions of saline, or aqueous solutions containing organic solevents, such as ethanol. Also suitable are emulsions, such as oil-in-water emulsions. Solid carriers include both nutritative carriers, such as sucrose or gelatin, and non-nutritative carriers, such as cellulose or talc. Such carriers, for example, permit formation of tablets containing a particular dose of the prodrug. Also included are carriers of the implantable-type which permit sustained-release of the prodrug.

Slow-release capsules and other protective mediums are suitable for the oral administration of the compounds of the invention due to the protection afforded against hydrolysis in the gastrointestinal tract. Preferred are those capsules which permit the compounds to bypass the stomach. When the present compounds are to be administered peritoneally, they can be administered by subcutaneous, intramuscular or intravenous injections.

Amounts of the compounds of the invention useful for promoting the uptake of the drug by the brain may vary from individual to individual, as well as varying from the particular disorder being treated and the particular effect desired. Such amounts can be determined by experimentation as is well understood by those skilled in the pharmaceutical arts. For suppressing appetite with Dopamine conjugates, amounts in the range of about 100–20000 micro grams per kilogram body weight are preferred.

Generally, compounds are most active when administered intravenously than by the other preferred routes. However, when an amide bond is used to conjugate the drug and carrier, oral administration of the drug appears to work quite well. In any event, when the conjugates of the invention are used to promote the uptake of a drug into the central nervous system, they are administered to humans in amounts sufficient to promote the crossing of the blood brain barrier. When the therapy involves restoring a deficiency of a neuro-transmitter in a human, the conjugate is administered in an amount sufficient to cause the normalization of the deficiency. When the compounds of the present invention are used for treating Parkinsonism or hyperprolactinemia or for suppressing appetite, then they are administered to a human in need of such treatment in an amount sufficient to affect the desired result.

Administration, of course, may be made by any method which allows the active compound to reach the bloodstream and penetrate through the blood brain barrier. Typical methods include oral, rectal, peritoneal and topical administration of the compounds. When the compounds are administered orally, the composition can be in the form of dragees, tablets, syrups or ampules. When the compounds are administered rectally, the composition can be in the form of a suppository. In addition, when the compounds of the invention are to be administered by topical application, they can be in the form of pomade or a gel.

The ability of the bond between the drug and the carrier to be broken once the prodrug is in the CNS will influence the choice of bonds. Likewise, the desired delivery site in the CNS may affect the choice of bonds as the enzymes responsible for breaking various bonds are concentrated in particular locations.

Variations of the particular carrier described in the preferred embodiment also are contemplated. For example, it has been found that a straight chain fatty acid that does not occur naturally in the brain and having 12 carbon atoms and no double bonds coupled to dopamine does not effectively cross the blood brain barrier and is completely inactive as an appetite-suppressant. Likewise, another straight chain fatty acid that does not occur naturally in the brain and having 22 carbon atoms and no double bonds coupled to dopamine does not effectively cross the blood brain barrier and is essentially inactive as an appetite-suppressant. However, a straight chain fatty acid occurring naturally in the brain and having 18 carbon atoms and 3 double bonds coupled to dopamine is partially active. This molecule crosses the blood brain barrier, and it has some effect on locomotor activity although no substantial effect on appetite. Thus, it appears that the length of the fatty acid, the degree of saturation and whether the fatty acid is naturally occurring in the brain affects the ability of the carrier to be combined with a drug to form a prodrug that will cross the blood brain barrier and effectively deliver and liberate the drug at an active site. The carrier molecule preferably is a straight-chained fatty acid of between 16 and 26 carbon atoms in length. More preferably the carrier molecule is between 16 and 22 carbon atoms in length and occurs naturally in the brain. Among the fatty acids occurring naturally in the brain are those with 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). While the position of the double bonds may be between any of the carbon atoms in the fatty acids, the preferred loci are those which occur naturally in the fatty acids of the CNS. Among the naturally-occurring fatty acids, C16:0 and C22:6 are preferred due to their preference for concentrating in the synaptosomal membranes, with C22:6 most preferred. It also has been found that C18:3 acts above average in its ability to deliver a compound across the blood brain barrier.

The fatty acids of this invention include both substituted and unsubstituted fatty acids. In the substituted fatty acid, at least one hydrogen along the fatty acid chain is replaced with a substituent. Examples of such substituents include alkyl groups, e.g. methyl, ethyl, propyl, isopropyl, butyl, and pentyl. Only those substituents that do not greatly adversely effect the ability of the carrier to perform its intended functions, including crossing the blood brain barrier and/or targeting the drug to a particular area of the brain, e.g. $D_2$ receptors, can be used. In addition to the foregoing fatty acids, branched chain fatty acids having between 16 and 26 carbon atoms may be used. Particular examples include analogues of the naturally-occurring polyisoprenoids (dolicols) such as

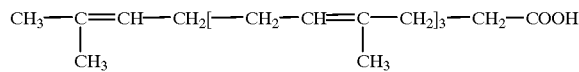

This invention further pertains to methods for introducing a drug into the central nervous system. The method comprises introducing a pharmaceutically effective amount of the prodrugs described above into the bloodstream of a patient. A pharmaceutically effective amount is that amount necessary to prevent, treat, or reduce the symptoms associated with a particular condition or disease being treated.

This invention also pertains to methods for manufacturing pharmaceutical preparations, including coupling a fatty acid to a drug to form a prodrug, and then forming a pharmaceutical dose containing the prodrug and a pharmaceutically acceptable carrier.

Having now fully described this invention, it will be appreciated by those of ordinary skill in the art that the same can be practiced with a wide and equivalent range of compositions, modes of administration, therapeutic treatments and the like, without affecting the spirit or scope of the invention or any embodiment thereof.

What is claimed is:

1. A compound comprising:
   a fatty acid coupled to an anticancer agent selected from the group consisting of methotrexate, cisplatin, prednisone, hydroxyprogesterone caproate, medroxyprogesterone acetate, megestrol acetate, diethylstilbestrol, ethinyl estradiol, tamoxifen, testosterone propionate, fluoxymesterone, vinblastine (VLB), vincristine, vindesine, etoposide, teniposide, dactinomycin (actinomycin D), daunorubicin (daunomycin; rubidomycin), doxorubicin, bieomycin, plicamycine (mithramycine), mitomycin (mitomycin C), -asparaginase, hydroxyurea, procarbazine (N-methylhdrazine, MIH), mitotane, aminoglutetimide, mechlorethamine, cyclophosphamide, melphalan (-sarcolysin), chlorambucil, busulfan, carmustine (BCNU), lomustine (CCNU), semustine (methyl-CCNU), streptuzocin (steptozotocin), dacarbazine (DTIC: dimethyltriazenomidazolecarboxamide), methotrexate (amethopterin), cytarabine (cytosine arabinoxide), mercaptopurine (6-mercaptopurine: 6-MP), thioguanine (6-thioguanine: TG).

2. The compound of claim 1, wherein the fatty acid is selected from the group consisting of C16:0; C16:1; C16:2; C18:1; C18:2; C18:3; C20:1: C20:2; C20:3; C20:4; C22:4; C22:5; C22:6; and C24:4.

3. The compound of claim 1, wherein the fatty acid is C16:0.

4. The compound of claim 1, wherein the fatty acid is C16:1.

5. The compound of claim 1, wherein the fatty acid is C16:2.

6. The compound of claim 1, wherein the fatty acid is C18:1.

7. The compound of claim 1, wherein the fatty acid is C18:2.

8. The compound of claim 1, wherein the fatty acid is C18:3.

9. The compound of claim 1, wherein the fatty acid is C20:1.

10. The compound of claim 1, wherein the fatty acid is C20:2.

11. The compound of claim 1, wherein the fatty acid is C20:3.

12. The compound of claim 1, wherein the fatty acid is C20:4.

13. The compound of claim 1, wherein the fatty acid is C22:4.

14. The compound of claim 1, wherein the fatty acid is C22:5.

15. The compound of claim 1, wherein the fatty acid is C22:6.

16. The compound of claim 1, wherein the fatty acid is C24:4.

17. A pharmaceutical preparation containing the compound of claim 1 and a pharmaceutically-acceptable carrier.

18. A pharmaceutical preparation containing the compound of claim 2 and a pharmaceutically-acceptable carrier.

* * * * *